(12) United States Patent
Fujimoto

(10) Patent No.: US 6,884,811 B2
(45) Date of Patent: Apr. 26, 2005

(54) ANTIFUNGAL COMPOSITION

(75) Inventor: Kazuhide Fujimoto, Kawanishi (JP)

(73) Assignee: Shinto Fine Co., Ltd., Osaka (JP)

(*) Notice: Subject to any disclaimer, the term of this patent is extended or adjusted under 35 U.S.C. 154(b) by 101 days.

(21) Appl. No.: 10/231,207

(22) Filed: Aug. 30, 2002

(65) Prior Publication Data
US 2003/0114506 A1 Jun. 19, 2003

(30) Foreign Application Priority Data
Sep. 4, 2001 (JP) .......................... 2001-266762

(51) Int. Cl.⁷ .................. A01N 43/64; A01N 43/78; A01N 43/50; A01N 43/52
(52) U.S. Cl. .................. 514/359; 514/183; 514/359; 514/365; 514/369; 514/372; 514/385; 514/393; 514/394; 514/395
(58) Field of Search ................. 514/183, 359, 514/365, 369, 385, 393, 394, 395, 372, 479

(56) References Cited

U.S. PATENT DOCUMENTS 5,185,357 A   2/1993  Inui ..................... 514/372

FOREIGN PATENT DOCUMENTS

| JP | 63-41405 | 2/1988 |
| JP | 6-164803 | 6/1990 |
| JP | 7-133205 | 5/1995 |

OTHER PUBLICATIONS

Oguma, Akira et al. (DN 131:166501, HCAPLUS, abstract of JP 11228302).*

* cited by examiner

Primary Examiner—Sabiha Qazi
(74) Attorney, Agent, or Firm—Birch, Stewart, Kolasch & Birch, LLP

(57) ABSTRACT

An antifungal composition comprising 3-iodo-2-propynyl butylcarbamate, 4,5-dichloro-2-octyl-isothiazolin-3-one and methyl 2-benzimidazolylcarbamate is useful as industrial antifungal composition, particularly for wood protection.

6 Claims, No Drawings

ANTIFUNGAL COMPOSITION

FIELD OF THE INVENTION

This invention relates to antifungal compositions, mainly for industrial use, such as paints, adhesives, sealing agents, inks, woods, leathers, fibers, etc., more particularly for wood protection.

BACKGROUND ART

Heretofore, halogenated phenol compounds or organotin compounds were frequently used as active ingredients of industrial antifungal agents. However, these compounds have high acute toxicity as well as in chronic toxicity and also are relatively hard to be decomposed. And there is a fear for a secondary environmental pollution caused by accumulation of said compounds in the antifungal agents containing the same. Accordingly, these compounds have now come to be unsuitable for use. On that account, antifungal agents which are higher by far in safety have come to be developed enthusiastically, and 3-iodo-2-propynyl butylcarbamate (hereinafter, referred as to IPBC) etc. are used for controlling fungi of paints, woods and so on. However, as IPBC has antifungal activity against limited species of fungi, it is difficult to acquire a sufficient efficacy for using said compound solely. So, necessary amount of IPBC for satisfying the purpose becomes sometimes high, and then it is not economical. 4,5-Dichloro-2-octyl-isothiazolin-3-one (hereinafter referred as to COIT) and methyl 2-benzimidazolylcarbamate (hereinafter, referred as to BCM) are known as industrial antifungal agents with high safety. When such agent is solely used, fungicide resistance has often developed and high concentration is required to get sufficient efficacy. So, such compound is deficient for industrial antifungal agent.

In order to solve such problems, a lot of attempts such as the combination of various fungicides, the expansion of fungicidal spectrum and the increasing of antifungal activity have been conducted. In general, the combination shows the fungicidal activity of each compound or merely additive activity of each compound. For example, JP sho-63-41405A demonstrates the use of sodium 1,4-bis(2-ethylhexyl) sulfosuccinate as the stabilizer of IPBC. JP hei-2-164803A demonstrates the combination of IPBC with benzimidazole compounds. However, the combination did not show the synergistic activity, and the antifungal activity was not sufficient. JP hei-3-251508A demonstrates the combination of benzimidazole compounds with isothiazoline compounds, and JP hei-7-133205A demonstrates the combination of COIT and IPBC. However, as the fungus species not to be controlled by these combinations have occurred, developing more effective antifungal compositions are desired.

This invention was made to solve above-mentioned problems, and an object of the invention is to provide industrial antifungal compositions which have excellent antifungal activities as well as excellent broad spectrum against a wide variety of species of fungi.

SUMMARY OF THE INVENTION

The present invention provides the antifungal composition containing three compounds of IPBC, COIT and BCM as its active ingredients. The inventor found that the combination of three compounds comprised of IPBC, COIT and BCM showed significantly high synergistic antifungal activity in comparison with that of each compound or the combination of two of them,

DETAILED DESCRIPTION OF THE INVENTION

The industrial antifungal compositions of the present invention are illustrated below in detail.

IPBC, COIT and BCM utilized as active ingredients in the present invention are known compounds and available on the market.

According to the purpose for which they are used, the antifungal compositions of the present invention are applicable directly to the, objects to which they are applied, or they are applicable thereto after having been formed into various formulations such as oil, emulsifiable concentrate, paste, flowable type formulations. Polar solvents to be used for the formulation are glytols such as ethylene glycol, propylene glycol, diethylene glycol, triethylene glycol, dipropylene glycol, hexylene glycol and polyethylene glycol; glycol ethers such as diethylene glycol monomethyl ether, diethylene glycol monoethyl ether and diethylene glycol monobutyl ether; alcohols such as isopropyl alcohol and ethyl alcohol; dimethylacetamide; dimethylsulfoxide; γ-butyrolactone; methylethylketone and water. Such solvents are used independently or by mixing two or more.

Non-polar solvents to be used for the formulation are plasticizer (e.g. dioctyl phthalate and diisononyl phthalate), xylene, toluene, isophorone, phenylxylylethane, diethylene glycol monobutyl ether acetate, propylenecarbonate, liquid paraffin, kerosene, coconut oil, rape seed oil, cotton seed oil, castor oil or soybean oil. Such solvents are used independently or by mixing two or more.

Two or more polar solvents and non-polar solvents can be mixed. The surfactants can be used if necessary. If used, nonionic surfactants, anionic surfactants, cationic surfactants or amphoteric surfactants can be selected.

Nonioic surfactants, such as polyoxycthylene alkylphenyl ether, polyoxyethylene styrylphenyl ether, polyoxyethylene alkyl ether, sorbitan fatty acid ester, polyoxyethylene sorbitan fatty acid ester, etc., anionic surfactants, such as sulfate salts of alkylbenzene, sulfate salts of polyethylene alkyl ether, sulfate salts of polyethylene alkylphenyl ether, dialkylsulfosuccinate, etc., cationic surfactants such as salts of aliphatic amine, tertiary ammonium salts, etc. and amphoteric surfactants such as betaine type surfactant, salts of aminocarboxylic acid, etc. are used, but not limited to them. Two or more nonionic surfactants, anionic surfactants, cationic surfactants and amphoteric surfactants can be used simultaneously.

The proportion of each compound used in the industrial antifungal compositions of the present invention may be varied, but usually set at the mixing ratio to be given synergistic effect. The mixing ratio of IPBC to COIT is 10:1 to 1:10, preferably 5:1 to 1:5 by weight, and the mixing ratio of the total of IPBC and COIT to BCM is 10:1 to 1:10, preferably 5:1 to 1:5 by weight.

The antifungal compositions of the present invention are applied to wood for antifungal use. Further, the antifungal compositions of the present invention are applied to paint for providing antifungal efficacy. The application amount is suitably set, but usually 0.001 to 1 g/m$^2$, preferably 0.005 to 0.2 g/m$^2$ of wood surface or 0.001 to 1%, preferably 0.01 to 0.4% of paint as the total active ingredients.

The antifungal compositions of the present invention are applicable combined with various industrial materials and products, for example, fungicides, bactericides, insecticides, anticorrosive agents and stabilizers, etc.

EXAMPLES

The following examples and comparable examples of the present invention are set forth, by way of illustration but not of limitation. In these examples, percentages and parts are by weight unless specified otherwise.

Examples 1 to 3 and Comparable Examples 1 to 6

The antifungal composition of examples 1 to 3 and the comparable examples 1 to 6 are shown in Table 1. In case of comparable examples 1, 2 and 4, each component was mixed and stirred thoroughly, and then antifungal compositions were formulated. In case of examples 1 to 3 and the comparable examples 3, 5, and 6, each component shown was mixed, crashed, with glass beads 1 mm in diameter in a pearl mill for 15 minutes, and then filtrated by a wire net. The antifungal compositions were obtained.

TABLE 1

|  | Example 1 | Example 2 | Example 3 | Comparable example 1 | Comparable example 2 | Comparable example 3 | Comparable example 4 | Comparable example 5 | Comparable example 6 |
|---|---|---|---|---|---|---|---|---|---|
| IPBC | 2 | 3 | 2 | 10 |  |  | 5 | 5 |  |
| COIT | 2 | 3 | 4 |  | 10 |  | 5 |  | 5 |
| BCM | 6 | 4 | 4 |  |  | 10 |  | 5 | 5 |
| Surfactant | 10 | 10 | 10 | 10 | 10 | 10 | 10 | 10 | 10 |
| Solvent | 60 | 60 | 60 | 60 | 60 | 60 | 60 | 60 | 60 |
| Water | 20 | 20 | 20 | 20 | 20 | 20 | 20 | 20 | 20 |

Surfactant: polyoxyethylene styrylphenyl ether
Solvent: propylene glycol

Test Example 1 Antifungal Activity Against Fungus on Wood

As sapwood of Scotch pine (2 cm width×5 cm length×0.3 cm thick) was dipped for 30 seconds in the predetermined diluted solutions of each formulation, followed by air drying. This specimen was placed on a potato dextrose agar plate, and 1 ml of a mixed fungus spore was sprayed over the spepimen, followed by culturing at 28 degree C and 95% RH for 28 days, and observed at every 7 days. The test strains used were *Aspergillus niger, Penicillium funiculosum, Aureobasidium pullulans, Gliocladium virens, Cladosporium cladosporioides* and *Neurospora* sp. The results obtained are shown in Table 2. In the table, the degree of fungus growth was determined according to the following ratings.

(−) No fungus growth is observed at all on the specimen.
(+) The area of the specimen on which fungus have grown on only the side
(++) The area of the specimen on which fungus have grown is equal or less than ⅓ of the total area of said specimen.
(+++) The area of the specimen on which fungus have grown exceeds ⅓ of the total area of said specimen.

TABLE 2

| | | Antifungal efficacy on wood | | | |
|---|---|---|---|---|---|
| | Conc. | Days after treating | | | |
| Example | (%) | 7 days | 14 days | 21 days | 28 days |
| Untreated |  | +++ | +++ | +++ | +++ |
| Example 1 | 0.25 | − | − | − | − |
|  | 0.5 | − | − | − | − |
| Example 2 | 0.25 | − | − | − | − |
|  | 0.5 | − | − | − | − |
| Example 3 | 0.25 | − | − | − | − |
|  | 0.5 | − | − | − | − |
| Comparable example 1 | 0.25 | − | + | +++ | +++ |
|  | 0.5 | − | + | + | ++ |
| Comparable example 2 | 0.25 | − | + | +++ | +++ |
|  | 0.5 | − | + | ++ | +++ |
| Comparable example 3 | 0.25 | − | + | +++ | +++ |
|  | 0.5 | − | + | ++ | +++ |
| Comparable example 4 | 0.25 | − | − | + | ++ |
|  | 0.5 | − | − | + | ++ |
| Comparable example 5 | 0.25 | − | − | + | ++ |
|  | 0.5 | − | − | − | + |
| Comparable example 6 | 0.25 | − | − | ++ | +++ |
|  | 0.5 | − | − | + | + |

As is clear from the results shown in Table 2, the antifungal compositions of the present invention showed an excellent efficacy in comparison with each component and the mixture of two components.

Test Example 2 Antifungal Activity on Emulsion Paint

An acrylic type emulsion paint (Page 70, a product of Shinto Paint Company, Limited) incorporated with a specified amount of the antifungal agent was uniformly coated on qualitative test filter paper in the same weight as of said filter paper and dried to prepare a specimen. The specimen was cut out at 30 mm in diameter, then immersed in 200 ml of ion exchanged water for 18 hours at the room temperature and dried. The specimen was placed on the glucose-peptone medium (glucose 40 g, peptone 10 g, agar 25 g, distilled water 1000 ml). One, milliliter (1 ml) of the mixed fungus spore of *Aspergillus niger, Penicillium funiculosum, Aureobasidium pullulans, Cliocladium virens* and *Cladosporium cladosporioides* was sprayed thereon. Thereafter, antifungal performance of the thus incorporated antifungal composition was evaluated in accordance with the test method of paint as described in "Methods of Test for Fungus Resistance" stipulated in JIS Z 2911. The results obtained are shown in Table 1. In the table, the degree of fungus growth was determined according to the following ratings.

(−) No fungus growth is observed at all on the specimen.
(+) The area of the specimen on which fungus have grown does not exceed 1/10 of the total area of said specimen.
(++) The area of the specimen on which fungus have grown is 1/10 to 1/3 of the total area of said specimen.
(+++) The area of the specimen on which fungus have grown exceeds 1/3 of the total area of said specimen.

TABLE 3

| Example | Conc. (%) | Days after treating | |
|---|---|---|---|
| | | 7 days | 14 days |
| Untreated | | +++ | +++ |
| Example 1 | 0.2 | − | − |
| | 0.4 | − | − |
| Example 2 | 0.2 | − | − |
| | 0.4 | − | − |
| Example 3 | 0.2 | − | − |
| | 0.4 | − | − |
| Comparable example 1 | 0.2 | + | +++ |
| | 0.4 | + | ++ |
| Comparable example 2 | 0.2 | + | ++ |
| | 0.4 | + | ++ |
| Comparable example 3 | 0.2 | + | +++ |
| | 0.4 | − | + |
| Comparable example 4 | 0.2 | + | ++ |
| | 0.4 | − | + |
| Comparable example 5 | 0.2 | + | ++ |
| | 0.4 | − | + |
| Comparable example 6 | 0.2 | + | ++ |
| | 0.4 | − | − |

As is clear from the results shown in Table 3, the antifungal compositions of the present invention showed an excellent efficacy in comparison with each component and the mixture of two components.

What is claimed is:

1. An antifungal composition which comprises a synergistic effective amount of 3-iodo-2-propynyl butylcarbamate, 4,5-dichloro-2-octyl-isothiazolin-3-one and methyl 2-benzimidazolylcarbamate as active ingredients.

2. An antifungal composition according to claim 1, wherein the mixing ratio of 3-iodo-2-propynyl butylcarbamate to 4,5-dichloro-2-octyl-isothiazolin-3-one is in the range of 10:1 to 1:10 by weight and the mixing ratio of the mixture of 3-iodo-2-propynyl butylcarbamate and 4,5-dichloro-2-octyl-isothiazolin-3-one to methyl 2-benzimidazolylcarbamate is in the range of 10:1 to 1:10 by weight.

3. A method for controlling fungus which comprises applying to wood an effective amount of the composition described in claim 1.

4. A method for controlling fungus which comprises applying to wood an effective amount of the composition described in claim 2.

5. A method for providing antifungal efficacy which comprises applying to paint an effective amount of the composition described in claim 1.

6. A method for providing antifungal efficacy which comprises applying to paint an effective amount of the composition described in claim 2.

* * * * *